United States Patent [19]

Handelsman et al.

[11] Patent Number: 5,618,692

[45] Date of Patent: Apr. 8, 1997

[54] ZWITTERMICIN RESISTANCE GENE AND BIOCONTROL BACTERIA WITH THE GENE

[75] Inventors: Jo Handelsman; Jocelyn L. Milner; Elizabeth A. Stohl; Sandra J. Stewart; Eric Stabb, all of Madison, Wis.

[73] Assignee: Wisconsin Alumni Research Foundation, Madison, Wis.

[21] Appl. No.: 304,076

[22] Filed: Sep. 12, 1994

Related U.S. Application Data

[63] Continuation-in-part of Ser. No. 207,335, Mar. 8, 1994, abandoned, which is a continuation-in-part of Ser. No. 878,800, May 5, 1992, abandoned, which is a continuation-in-part of Ser. No. 758,644, Sep. 12, 1991, abandoned, which is a division of Ser. No. 194,399, May 16, 1988, Pat. No. 5,049,379, which is a continuation-in-part of Ser. No. 77,850, Jul. 22, 1987, abandoned.

[51] Int. Cl.$^6$ .......................... C07H 21/04; C12P 21/00; C12N 15/63
[52] U.S. Cl. .................. 435/69.1; 435/172.1; 435/172.3; 536/23.7; 536/24.1
[58] Field of Search ................ 536/23.7, 24.1; 435/69.1, 172.1, 172.3

[56] References Cited

U.S. PATENT DOCUMENTS

| | | |
|---|---|---|
| 3,992,528 | 11/1976 | Graham . |
| 4,249,317 | 3/1981 | Vesely et al. . |
| 4,250,170 | 2/1981 | Kawaguchi et al. . |
| 4,877,738 | 10/1989 | Handelsman et al. . |
| 4,878,936 | 11/1989 | Handelsman et al. . |
| 5,049,379 | 9/1991 | Handelsman et al. . |

FOREIGN PATENT DOCUMENTS

| | | |
|---|---|---|
| 0193608 | 9/1986 | European Pat. Off. . |
| 0304178 | 2/1989 | European Pat. Off. . |
| WO8800966 | 2/1988 | WIPO . |

OTHER PUBLICATIONS

Buchanan, R.E. and N.E. Gibbons, *Bergey's Manual of Determinative Bacteriology*, 8th Ed., pp. 532–535 (1974).
Hutchins, A.S., "An In Vitro Inhibition of Root Rot Pathogens *Phellinus weiri, Armullariella mellea, Formes annosus*, and *Phytophthora cinnamomi* by a Newly Isolated *Bacillus* sp.," *Microb. Ecol.* 6(3):252–259 (1980).
Wakayama, et al., "Mycocerein, A Novel Antifungal Peptide Antibiotic Produced by *Bacillus cereus*," *Antimicrobial Agents Chemotherapy*, 26:6:939–940 (1984).
Kamicker, B.J. and W. Brill, "Identification of *Bradyrhizobium Japonicum* Nodule Isolates From Wisconsin Soybean Farms," *Applied Environmental Microbiology* 51:3:487–492 (1986).
Gurusiddaiah, S. et al., "Characterization of an Antibiotic Produced by a Strain of *Pseudomonas Fluorescens* Inhibatory to Gaeumannomyces Graminisvar. tritici and Pythium spp.," *Antimicrobial Agents and Chemotherapy* 29:3:488–495 (1986).
Misaghi, I.J., et al., "Fungistatic Activity of Water–Soluble Fluorescent Pigments of Fluorescent Pseudomonads," *Phythopathology* 72:1:33–35 (1982).

(List continued on next page.)

*Primary Examiner*—Stephanie W. Zitomer
*Assistant Examiner*—Paul B. Tran
*Attorney, Agent, or Firm*—Quarles & Brady

[57] ABSTRACT

A new gene from *Bacillus cereus* has been characterized which codes for a protein conferring resistance to the antibiotic zwittermicin A produced by some strains of the bacteria. The resistance gene, designated zmaR, is found to be present in almost all strains of the bacteria which are known to natively have the ability to synthesize zwittermicin A, and thus allows tests for the presence of the gene to serve as a test to be used with new strains to assay for zwittermicin A production. The gene also has use in increasing production of the

OTHER PUBLICATIONS

Howell, C.R. and R.D. Stipanovic, "Suppression of *Pythium ultimum*–Induced Damping–Off of Cotton Seedlings by *Pseudomonas fluorescens* and its Antibiotic Pyoluteorin," *Phytopathology* 70:8:712–715 (1980).

Howell, D.R. et al., "Control of *Rhrizoctonia solani* on Cotton Seedlings with *Pseudomonas fluorescens* and With Antibiotic Produced by the Bacterium," *Phytopathology* 69:4:480–482 (1979).

Plazinski, J. and B. G. Rolfe, "Influence of Azospirillum Strains on the Nodulation of Clovers by Rhizobium Strains," *Applied and Environmental Microbiology* 49:4:984–989 (1985).

Handelsman, "Abstract" on the Isolation of *Bacillus cereus* presented at a meeting on or after Jul. 26, 1986.

Yahalom, E., et al., "Azospirillum Effects on Susceptibility to Rhizobium Nodulation and on Nitrogen Fixation of Several Forage Legumes," *Can. J. Microbiol.* 33:510–514.

Handelsman, et al., "Zoospore Lysis in Biocontrol of *Phytophthora megasperma* by *Bacillus cereus* U.W. 85" Dept. of Plant Pathology, University of Wisconsin, Madison, WI 53705 (Published Aug. 1987).

Handelsman, J. et al., "Biological Control of Damping–off of Alfalfa Seedlings With *Bacillus cereus* UW86," *Applied and Environmental Microbiology* 56:3:713–718 (Mar. 1990).

Halverson, L.J. and J. Handelsman, "Enhancement of Soy Bean Nodulation by *Bacillus cereus* UW85 in the Field and a Growth Chamber," *Applied and Environmental Microbiology* 57:9:2767–2770 (Sep. 1991).

Halverson, L.J. and J. Handelsman, "Stability of Antibiotic–Resistance Markers in *Bacillus cereus* UW85," *The Rhizosphere and Plant Growth*, 107 (D.L. Keister and P.B. Cregan eds., Kluwer Academic Publishers (1991).

Goodman, R.M. and J. Handelsman, "Concerted Use of Transgenes and a Biocontrol Agent in Suppression of Diseases in Plants," Poster presented at Midwest Plant Biotechnology Consortium, Indianapolis, IN, Nov. 13–14, 1991 (Draft).

Handelsman, J., et al., "Microassay for Biological and Chemical Control of Infection of Tobacco by *Phytophthora parasitica* var. nicotianae," *Current Microbiology* 22:317–319 (1991).

Campbell, R. and A. Clor, "Soil Moisture Affects the Interaction Between *Gaeumannomyces graminis* var. tritici and Antagonistic Bacteria," *Soil. Biol. Biochem.* 17:4:441–446 (1985).

Phipps, P.M., "Evaluation of Biological Agents for Control of Sclerotinia Blight of Peanuts," *B and C Test* 7 (1992).

Miller, S.A., "Cytological and Biochemical Factors Involved in the Susceptible, Host Resistant and Non–host Resistant Interactions of Alfalfa," Ph.D. Thesis, University of Wisconsin, p. 48 (1982).

Oki, et al., *J. Antibiot.* (Tokyo), 42:1749–44 and 1756–74.

Goto et al., *Tetrahedron Lett.* 23:1271, 1982.

Tschen et al., *Proc. Natl. Sci. Counc. Repub. China Part B Life Sci* 13, 258–261, 1989.

Goto et al., *Tetrahedron Lett.* 23:1271, 1982.

Gilbert, Gregory S. and Jennifer L. Parke, "Effects of an Introduced Bacterium on Bacterial Communities on Roots," *Ecology*, 74(3):840–854 (1993).

Halverson, et al., "Variable stability of antibiotic–resistance markers in *Bacillus cereus* UW85 in the soybean rhizosphere in the field," *Molecular Ecology* 2:65–78 (1993).

Halverson, et al., "Population Biology of *Bacillus cereus* UW85 in the Rhizosphere of Field–Grown Soybeans," *Soil Biol. Biochem.*, 25:485–493 (1993).

Smith, et al., "Suppression of Cottony Leak of Cucumber with *Bacillus cereus* Strain UW85," *Plant Disease* Feb. 139–142 (1993).

FIG. 1

The 1.2 kb SphI-BamHI fragment conferred zwittermicinA resistance on *E. coli* strains in either orientation when carried on a shuttle vector or on a pGEM vector.

ZWITTERMICIN RESISTANCE GENE AND BIOCONTROL BACTERIA WITH THE GENE

CROSS-REFERENCE TO RELATED APPLICATIONS

This application is a continuation-in-part of application Ser. No. 08/207,335 filed Mar. 8, 1994, now abandoned which was a continuation-in-part of application Ser. No. 07/878,800 filed May 5, 1992, now abandoned, which was a continuation-in-part of Ser. No. 07/758,644 filed Sep. 12, 1991, now abandoned, which was a divisional of Ser. No. 07/194,399 filed May 16, 1988, now U.S. Pat. No. 5,049,379, which was a continuation-in-part-of Ser. No. 07/077,850 filed Jul. 22, 1982, now abandoned.

TECHNICAL FIELD

The present invention relates to resistance genes for antifungal compounds derived from biocontrol bacteria originally found useful in combatting damping off and root rots in plants.

BACKGROUND OF ART

Certain plants, of which alfalfa, soybeans, and common beans are examples, suffer from disease conditions called "damping off" and "root rot." The symptoms of damping off include the desiccation and subsequent death of seedlings soon after germination. Root rot symptoms include chlorosis and wilt of leaves and yellow to brown lesions with diffuse margins on roots and stems. The lesions can eventually lead to girdling and subsequent root decay resulting in decreased robustness in the plant or even in death. Often plants suffering from root rot begin by showing such symptoms, which may be mistaken as symptoms of drought and starvation. Such plants may be more vulnerable than healthy plants to attack by other pathogens, which are then mistaken as the cause of the death of the plants.

Damping off and root rot are merely two different sets of symptoms caused by infection of the plant by the same fungi and, in particular, by members of the Phytophthora, Pythium, Aphanomyces, Rhizoctonia, and Fusarium genera. Thus, *Phytophthora megasperma* f. sp. *medicaginis* (now formally known as *Phytophthora medicaginis*, and referred to hereinafter as "Pmm") causes both damping off and root rot in alfalfa when soils are wet in most parts of the world where alfalfa is grown, and *Phytophthora meqasperma* f. sp. *glycinea* has been shown to cause root rot in soybeans under wet growing conditions. However, fungi from among the other genera listed also are believed to attack alfalfa and soybeans. Root rot in common beans is believed caused by a complex of fungi including members of more than one of the genera referred to.

In general, control of damping off and root rot has been attempted by breeding for resistant plants. However, completely resistant cultivars have not been developed such that damping off and root rot remain major causes of crop loss. This is especially true under chronically wet growing conditions or when the same crop is planted repeatedly in the same fields. Certain fungicides such as metalaxyl partially control root rot. However, such fungicides are fairly expensive. For some crops, such as alfalfa, their use is not economically feasible. Also, resistance of the fungi to the fungicides can develop rapidly.

"Biological control" is defined as pathogen control by the use of a second organism. Mechanisms of biological control are diverse. For example, certain enteric bacteria have been examined for their usefulness in biological control of root rot in alfalfa. It is believed that control is obtained by competition between the enteric bacteria and the fungi for space on the surface of the alfalfa roots. In contrast, a toxin produced by one species of bacteria may be used to control another species of bacteria that appears as a pathogen. Bacterially produced antibiotics are an example of such toxins. The toxin can be isolated from the species producing it and administered directly, as is the common procedure with penicillin, or the species itself may be administered under appropriate circumstances to produce the toxin in situ. Once identified, such toxins produced by soil-dwelling bacteria may have utility in diverse other areas as antifungal or antibiotic agents.

BRIEF SUMMARY OF THE INVENTION

The present invention is summarized in that a resistance gene to an antibiotic toxin from *Bacillus cereus*, the toxin designated as zwittermicin A, is characterized and identified below.

The present invention is further summarized in sequence data about the zwittermicin resistance gene, which permit convenient assays on new putative biocontrol Bacillus strains to determine if they produce zwittermicin.

The present invention is also directed toward the use of the new gene and the assay for its presence to identify new bacterial strains useful in the control of fungal plant disease.

Other objects, features and advantages of the present invention will become apparent from the following specification.

DETAILED DESCRIPTION OF THE PREFERRED EMBODIMENT

The present invention relates to a newly identified gene found in Bacillus strains encoding resistance to an antibiotic, and the use of that gene in screening and identifying additional strains of biocontrol bacteria strains. The discovery and characterization of this gene represents the next step in a multistage research trail beginning with the isolation of a first biocontrol strain, the characterization of the antibiotic agent produced by that strain and believed responsible for the biocontrol effect and then an investigation into the biochemical adaptation of the Bacillus to the production of the antibiotic. To proceed in logical order, the original biocontrol strain, and the characterization of the antibiotic agent, will be discussed first, followed by a description of the characterization of the resistance gene.

A) Isolation of ATCC 53522 (UW85)

The original bacterial strain was isolated from soil that exerts biological control over species of fungi responsible for damping off and root rot in plants. The strain has been deposited in the American Type Culture Collection, given the designation ATCC 53522, and shall hereinafter be referred to as "ATCC 53522." In published literature by the inventor group, the strain was also referred to as UW85. It was further discovered that certain mutants of ATCC 53522 also provide biological control comparable to that provided by ATCC 53522. These bacteria have been obtained in substantially pure cultures. A "substantially pure" culture shall be deemed a culture of a bacteria containing no other bacterial species in quantities sufficient to interfere with replication of the culture. In addition, it has been discovered that the biological control is exerted by means of a toxin produced by the disclosed bacterial strains.

ATCC 53522 and what are defined below as its "protecting" mutants, together with antibiotics produced thereby, inocula containing the bacteria or their antibiotics, and methods for protecting plants from damping off and root rot that utilize the bacteria or their toxins are the subject of an earlier patent appliction. Also, compounds found in supernatant fluid and other bacteria-free fluid and culture medium removed from a culture of ATCC 53522 or of its protecting mutants, have been found to be "protecting antibiotics," and have been the subject of earlier patent applications. These compounds have been so characterized as to be identifiable independent of their source in cultures of ATCC 53522, or its protecting mutants and, the two compounds shall be referred to herein by the coined terms "zwittermicin A" and "antibiotic B." The terms "zwittermicin A" and "zwittermicin" will be used here interchangeably to refer to the zwitterionic antibiotic produced by B. cereus ATCC 53522, or UW85. Another fraction from the supernatant fluid from a culture of B. cereus ATCC 53522 has been found biologically active, having a capability to lyse Pmm zoospores, but, as revealed below, this zoolysin active fraction does not have the antifungal activity of the antibiotics.

The method by which the biological control referred to in the preceding paragraph may be verified to exist is the "plant protection assay" detailed below. "Biological control" of fungi causing damping off and root rot shall be deemed to exist if, when an effective quantity of a biocontrol Bacillus culture, the antifungal toxin produced by them, Bacillus cereus antibiotic, or any other compound or molecule is placed in the soil or other growing medium in the immediate vicinity of the plant to be protected, a statistically significant reduction in the symptoms of damping off or root rot occurs. An "effective quantity" to combat damping off and root rot shall be that quantity sufficient to result in such a visibly significant reduction of symptoms. Clearly, if no quantity of a bacteria or any toxin or other compound is an effective quantity as so defined, that bacteria, toxin, or compound is not capable of exerting biological control over the fungi causing damping off and root rot.

ATCC 53522, its mutants, and a class of new Bacillus strains which can be found by the method described below, are capable of exerting biological control and shall sometimes be referred to collectively as "protecting" bacteria. The zwittermicin antibiotic and other toxins capable of exerting such biological control shall sometimes be referred to as "protecting" compounds or toxins. Plants, including seeds, seedlings, and mature plants, treated with such an effective quantity of protecting bacteria, their toxins, or Bacillus cereus antibiotic shall be referred to as "protected" from root rot or damping off.

ATCC 53522 was one of some 500 bacteria strains isolated from alfalfa roots and accompanying soil obtained from fields at the University of Wisconsin Experimental Farms at Arlington and Marshfield, Wisconsin, and from two private farms at Verona and Cross Plains, Wisconsin. The isolation, screening and demonstration of biocontrol activity of strain ATCC 53522, and its mutants, is described in the specification of U.S. Pat. No. 4,877,738, the specification of which is hereby incorporated by reference.

Of 500 isolates from the 4 sites in Wisconsin referred to above, only ATCC 53522 strain was originally identified as having the ability consistently to exert biological control of *Phytophthora megasperma* (Pmm) in Iroquois alfalfa, as evidenced by at least 20 separate experiments. The level of control was such that alfalfa seedlings subjected to such control under the conditions of the screening procedure were visually indistinguishable from alfalfa seedlings that had never been exposed to Pmm. ATCC 53522 has been classified as *Bacillus cereus*, based on physiological tests, its colony morphology, and its spore size, shape, and position. Thus, ATCC 53522 produces acetoin, forms acid from glucose broth, hydrolyzes starch, and grows in anaerobic agar. These characteristics, together with colony morphology, and spores size, shape, and position observed in ATCC 53522 are cited as distinctively characteristic of *Bacillus cereus* by R. E. Buchanan and N. E. Gibons, co-editors (1974), *Bergey's Manual of Determinative Bacteriology*, 8th Edition, pp. 532–535.

*Bacillus cereus* is a not uncommon bacterium in field soils. However, strains of *Bacillus cereus* demonstrating antifungal activity were generally unheard of prior to the identification of ATCC 53522. The inventors originally tested two known strains of *Bacillus cereus* obtained from entirely separate sources and found neither of them to exhibit the antifungal properties of ATCC 53522. Then, a method was derived to screen other field isolates for antibiotic production, and other such strains can now readily be found. In the original screening, however, of the 500 root-associated bacteria reviewed in the isolation process, many were probably *Bacillus cereus* and, in fact, many of them had the same colony morphology as ATCC 53522, but none of these other strains exhibited the antifungal qualities of ATCC 53522. S. Wakayama, et al. (1984), *Antimicrob. Agents Chemother.*, 26, 939–940, describe antifungal activity in a strain of *Bacillus cereus*. However, most of the antifungal antibiotics are made by *Bacillus subtilis*, which is easily distinguishable from ATCC 53522. The antifungal toxin produced by ATCC 53522 differs from that of the reported strain of *Bacillus cereus* referred to in that the toxin is of lower molecular weight and has different solubility properties. In addition, ATCC 53522 differs from the reported *Bacillus cereus* strain in that it grows anaerobically whereas the reported strain does not. Consequently, it is clear that the two *Bacillus cereus* strains are not the same and that their toxins are not the same.

B) Plant Protection Assay

The following is a disclosure of the plant protection assay whereby a test material such as a bacteria, an antibiotic, or the like, may be tested for its ability to exert biological control over a fungus capable of causing the symptoms of damping off or root rot. The seed of the plant to be protected is planted in a planting medium in the presence of damping off or root rot causing fungi. The planting medium may be a damp soil containing such fungi, vermiculite in water with the fungi present either in the vermiculite and water or in or on the seed or seedling, or any other planting medium in which the seed will grow and the fungi may freely develop, such as a laboratory or greenhouse agar-based formulation. The bacteria, antibiotic, or other test material is placed at least in the immediate vicinity of the seed. Such placement shall be understood to be in the "immediate vicinity" of the seed or seedling if any soluble test material or any soluble exudate of a bacteria being tested will be in actual contact with the germinating seedling.

Preferably the seed is coated with the test material, and when the test material is so used with respect to a seed, it shall be referred to hereinafter as a "seed inoculum." The process of coating seed with a seed inoculum is generally well known to those skilled in the art, and any conventional method that does not require conditions sufficiently harsh to kill bacteria or destroy toxins or other materials included in the seed inoculum is adequate. The plant seed to be protected is drenched in a broth culture of the bacteria and is mixed vigorously with it to coat the surface of the seed with the bacterial suspension. The seed may then be dried aseptically, preferably by being placed within a laminar flow hood on a sterile surface such as a sterile petri plate. The result is a dry, seed inoculum-coated seed. When the coated seed is planted in the planting medium, the test material accompanies it to reside in the immediate vicinity of the seed. Alternatively, the seeds can be pregerminated in water and then plated in the planting medium, after which the inoculum can be applied to the seedling.

After a time sufficient for seedling growth and the expression of the symptoms of damping off, seedlings developing from the planted seed or seedling may be evaluated for visual evidence of protection, when compared to controls. In strains of alfalfa, known to be vulnerable to damping off, 2 weeks of growing time in a growth chamber at 24° C. with a 12 hour photo-period was found to be a period sufficient for the expression of symptoms of damping off when seedlings were being grown in test tubes containing roughly $10^3$ to $10^4$ zoospores of Pmm or comparable, damping off-causing fungi. Protected seeds or seedlings developed into seedlings visually indistinguishable from uninfected seeds while control seedlings developing from unprotected seeds were killed.

C) Mutant strains

Protecting mutants of ATCC 53522, or any new biocontrol strain, include both naturally occurring and artificially induced mutants. For example, ATCC 53522 is generally sensitive to the antibiotics rifampicin and neomycin. However, naturally occurring mutants of ATCC 53522 were isolated that exhibited resistance to one or the other of these antibiotics. Certain of these mutants, as well as one naturally occurring mutant distinguishable from the parent ATCC 53522 strain by the appearance of its colonies, are discussed in the Examples below and were found to protect alfalfa plants in the plant protection assay. Other mutants of ATCC 53522 were artificially induced by subjecting ATCC 53522 to the mutagen N-methyl-nitrosoguanidine in conventional ways, as is discussed in the Examples below. Most of these induced mutants also were found to protect alfalfa plants in the plant protection assay.

Various mutagenesis studies have also been done on cultures of ATCC 53522 which have resulted in mutant colonies which are deficient in production of the antibiotics and which are deficient in biocontrol activity, as determined by the biocontrol assays described herein. Those mutant colonies also were deficient in antibiotic production. An analysis of the mutant colonies for both biocontrol activity and for antibiotic accumulation revealed that the interpretation that the biocontrol activity was associated with the accumulation of both antibiotics as zwittermicin A and antibiotic B was consistent with the data uncovered from the mutant strains. Residual disease suppressive activity was detected in some strains that lack detectible antibiotic production, and such suppressive activity may be due to the zoospore-lysis activity or to another agent. This observation is consistent with the fact that many biocontrol bacterial colonies may depend on multiple strategies for disease suppression and the data would thus suggest that the antibiotics are required, but not sufficient, for the full biological control of cultures. Nevertheless, the antibiotics may have independent utility in other environments for the control of bacterial or fungicidal agents, as described in more detail below.

D) Isolation and characterization of antibiotic agents

As has been disclosed above, it has been further discovered that active anti-root rot toxins, identified herein as the *B. cereus* antibiotics zwittermicin A and antibiotic B, are produced by ATCC 53522, other new Bacillus strains, and those of their mutants that are characterized by their abilities to protect plants from root rot in the plant protection assay. The two *Bacillus cereus* antibiotics may be collected from growth media in which the bacteria have been cultured and has been prepared in a substantially pure form. A preparation of *Bacillus cereus* antibiotic shall be deemed "substantially pure" if it is sufficiently free of interfering substances as to be able to be active to inhibit root rot by Pmm. The two *Bacillus cereus* antibiotics are effective to protect plants from damping off and root rot, even when separated from the bacteria producing it and applied to seed and to seedlings that have been placed in a planting medium containing root rot causing fungi. As is discussed below, the effectiveness of the application of two *Bacillus cereus* antibiotics is demonstrable by the plant protection assay, with the antibiotic being substituted for a protecting bacteria. Thus, the invention includes either or both antibiotics and a seed inoculum containing effective quantities of either *Bacillus cereus* antibiotic.

As has been disclosed above, the *Bacillus cereus* antibiotics may be isolated from ATCC 53522 by filtering the bacteria from the culture media in which they have been grown to a sporulated culture. Other conventional purification and concentration steps may then be undertaken as may be considered convenient or desirable, so long as the toxin remains active, as may be demonstrated by the plant protection assay.

Both of the antibiotics from *Bacillus cereus* described herein can be readily isolated from cultures of *Bacillus cereus* ATCC 53522 by culture of the bacteria and concentration of the resulting antibiotics from the culture supernatant. The supernatant can be fractionated in a column and then separated by electrophoresis to identify fractions which exhibit the biocontrol activity. It has been found that both antibiotics will stain with ninhydrin or silver nitrate.

The chemical formula and structure of the antibiotic zwittermicin A has been studied extensively. The molecular weight of a molecule, which was originally identified as *Bacillus cereus* antibiotic, was originally thought to be between 500 and 1000 daltons. Subsequent measurement of the molecular weight of purified antibiotic, now referred to a zwittermicin A, by mass spectroscopy revealed a molecular weight of about 396 daltons. The zwittermicin A antibiotic is soluble in methanol and insoluble in acetone, chloroform, and ethyl acetate. The antibiotic zwittermicin A moves as both an anion and a cation in an electric field, although it is a very weak anion. In repeated experiments, the antibiotic zwittermicin A has been tested for various protecting abilities by plant protection assays. The tests, some of which are discussed below, have revealed that the zwittermicin A antibiotic has proven useful antibiotic capabilities against Phytophthora and Pythium species as well as other fungal species. In addition, the antibiotic zwittermicin A also inhibits growth of some bacteria, notably *Erwinia herbicola*, several Pseudomonas species, and some *E. coli* strains.

Figure 1:
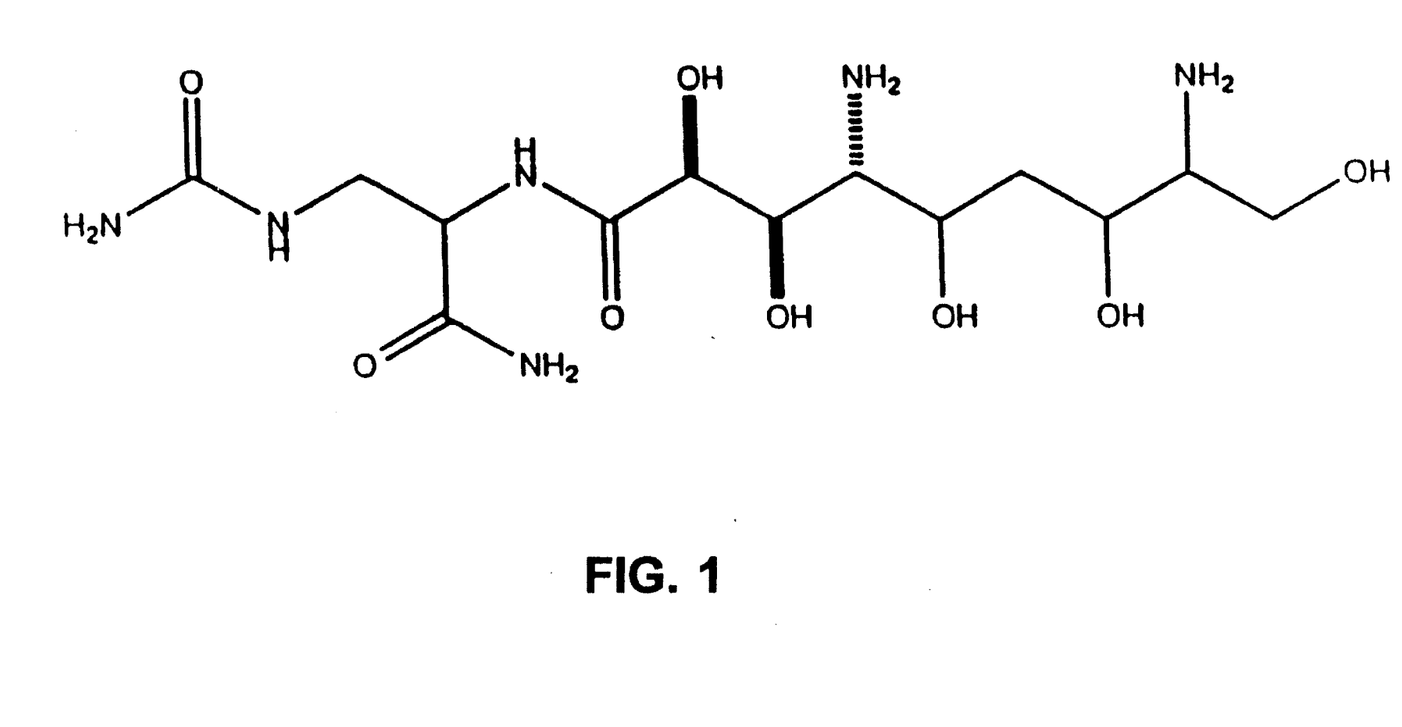
FIG. 1 is an illustration of the deduced chemical structure of zwittermicin A.

The chemical structure for the zwittermicin A molecule has been tentatively identified. Shown herewith in FIG. 1 is the deduced chemical structure of the molecule which has been identified. The molecule is an aminopolyol antibiotic which represents a new class of antibiotics isolated from Bacillus species. Zwittermicin A is a very weak acid, and will migrate as an anion at pH 9.2 as did other amide-containing compounds. It is appropriate to rely on biological activity as a detection method during purification or fractionation because the antibiotic zwittermicin A does not contain chromophores that can be detected spectrophotometrically.

The structure illustrated on FIG. 1 was determined by NMR and mass spectrometry studies of the native molecule, the acetylated derivative, and a hydrolysis product. While it is believed that this structure is correct, it is yet possible that there might be minor misplacements of smaller residues without affecting the overall chemical characterization or structure of the molecule. It is known, as described above, that the molecule is certainly a linear aminopolyol, a cation, and a very weak acid. The structure disclosed in FIG. 1 is consistent with that interpretation and is believed to be the correct molecular structure.

At this point, an incomplete structure is known for the antibiotic B. The antibiotic B also shows inhibitory activity in a biocontrol assay. The antibiotic B will also bind to CM-Sephadex or amberlite IRC-50 at pH 7.0 and will elute when the pH is raised above 10.0. The staining properties and nuclear magnetic resonance profile of antibiotic B indicates that it is an aminoglycoside. While the antibiotic B has a slightly narrower spectrum of antifungal and antibacterial activity than zwittermicin A it nevertheless exhibits reasonably broad antifungal and antibacterial efficacy.

As the examples below indicate, both zwittermicin A and antibiotic B have significant activity against a variety of pathogenic fungi and bacteria. As the data also indicate, not only are the antibiotics useful separately, they also have certain synergistic activities when used in combination with each other. It is believed that the antibiotics can be prepared by culture of the *Bacillus cereus* ATCC 53522, but can equally be recovered from a wide variety of other *Bacillus cereus* cultures. Described below is a plant protection assay developed to test plant protection activity as initially isolated using ATCC 53522. It is believed that that same assay can be used to test other candidate *Bacillus cereus* strains for biocontrol activity and it is believed that those strains would also make one or both of the antibiotic zwittermicin A or antibiotic B described herein.

The antibiotics may readily be isolated from colonies of bacteria which produce them, such as ATCC 53522 by recovering the supernatant from sporulating cultures of the microorganisms. The supernatant, as described above, can be fractionated in a column and then separated by electrophoresis to identify the fractions which exhibit the biocontrol activity. Using high voltage paper electrophoresis, the two molecules identified herein as zwittermicin A and antibiotic B can readily be repeatably recovered. At pH 9.2, the high voltage paper electrophoresis (HVPE) yields 2 spots which are associated with biocontrol activity. The first spot, associate with zwittermicin A, had a relative mobility ($R_f$) of 0.30 compared with orange G. The antibiotic B spot had an $R_f$ of 0.032. If the same HVPE process is conducted at pH 1.7, the relative mobilities of zwittermicin A and antibiotic B are $R_f$ 1.042 and -0.909 respectively.

As described below, both zwittermicin A and antibiotic B have a broad antibiotic activity against many fungal, and also some bacterial, pathogens. The activity extends not only to plant pathogens, but also to potential mammalian pathogens. It is also revealed from the data below, the level of toxicity for each individual pathogen varies over a significant range. Accordingly, the significant amount necessary to control a particular pathogen can be determined empirically by in vitro studies of the type described below. Based on such studies an "effective amount" can be determined for a particular target organism.

E) Identification and characterization of zwittermicin resistance

It was hypothesized that since the zwittermicin A antibiotic has broad antibacterial activity, as demonstrated by the data presented here, perhaps the strains which produced the antibiotic also possessed a genetic trait of resistance to the antibiotic. Accordingly, studies were conducted to determine if such a resistance trait could be identified in ATCC 53522. In essence, DNA fragments from *Bacillus cereus* ATCC 53522 were isolated from cultures of the native bacillus, and transformed into antibiotic-sensitive *E. coli* strains. The transformed *E. coli* strains were challenged with zwittermicin A. This research ultimately demonstrated that ATCC 53522 harbored at least one genetic trait, here termed zmaR, which conditions for resistance to zwittermicin A. The zmaR gene has been characterized and sequenced, as disclosed below. The transformation of the zmaR gene into sensitive bacterial strains which will express the gene has the effect of converting those strains into zwittermicin resistant strains. The protein produced by zmaR, here termed ZmaR is only yet tentatively characterized.

The identification and characterization of the zwittermicin resistance gene suggests several immediate applications for its use. First, most simply, the zmaR resistance gene is now made available for use as a selectable marker system for studies of bacterial genetics and for recombinant genetic experiments and procedures. Secondly, and probably more significantly, the availability of nucleotide sequence information about the zmaR gene enables rapid and easy assays for its presence in novel bacterial isolates from the environment. Since the presence of the zmaR gene, or other resistance determinant, is required for survival by strains which also produce the antibiotic, this information makes possible several possible ready, efficient, and rapid molecular procedures to screen newly isolated Bacillus strains for biocontrol activity, in general, and zwittermicin A production in particular. The zmaR gene may possibly also be used to enhance the zwittermicin A production characteristics of existing zwittermicin A producing Bacillus strains.

Set forth in SEQ ID: NO:1 below is the complete nucleotide sequence for the zmaR gene containing DNA fragment derived from *Bacillus cereus* strain ATCC 53522. Shown in SEQ ID: NO:2 below is the deduced amino acid sequence deduced from the largest open reading frame the nucleotide sequence of SEQ ID: NO:1, and which may be the ZmrA protein. The characterization of the gene, and the genetic manipulations for deriving the nucleotide sequence are described in greater detail below, in the examples. The DNA sequence encoding the zmaR gene has been compared with the data base of the National Center for Biotechnology Information (NCBI) for sequence analysis and comparison. The NCBI data base did not contain a DNA sequence or sequences with significant similarity to the zmaR sequence, using the BLASTN computer software analysis. Comparison of putative open reading frames of the zmaR gene to others contained within the data base reveal a 32% identity, and a 58% similarity by conserved substitutions of the amino acid sequence, to the tetracycline efflux pump proteins of *Bacillus subtilis*. The tetracycline efflux pump proteins of *B. subtilis* function to provide resistance to tetracycline in strains expressing these proteins by their active transport of tetracycline out of the cellular cytoplasm. It is therefore logical to assume that the zmaR gene encodes a protein having a similar functionality in *B. cereus*. Separately, it has been verified that the zmaR gene does not confer tetracycline resistance on *E. coli*, and hence does not encode a tetracycline efflux pump. The fact that zmaR confers resistance to zwittermicin A, combined with the similarity in amino acid sequence to the tetracycline efflux pump, suggests that the zmaR gene encodes a zwittermicin A efflux pump protein which provides resistance to the antibiotic effects of zwittermicin A by maintaining a low intracellular concentration of zwittermicin A, through active transport of zwittermicin A across the cell membrane out of the cell.

The function of the zmaR gene in serving as an efflux pump for zwittermicin A suggests, in turn, two immediate utilities for this protein in manipulating bacterial genetics. The first is, of course, to use the zmaR gene to confer resistance to the antibiotic zwittermicin A. The DNA sequence and putative amino acid sequence, described below, enables molecular biologists of ordinary skill in the art to use the DNA fragment sequence, in particular, by placing it in an expression vector for an appropriate host, and transforming it into a suitable host to express the ZmaR protein. The full length native genomic copy of zmaR from *B. cereus* can be used in hosts which recognize the native promoter, such as Bacillus species and *E. coli*, or the protein coding DNA sequence only can be joined to heterologous promoters to control its expression. The second immediately suggested utility would be to insert additional copies of zmaR gene into *B. cereus* strains which already have the capability to synthesize zwittermicin A. An over-expression of the zwittermicin A efflux pump in transformed *B. cereus* cells would increase pumping ability from the cells, and would relieve any feed back regulation which might otherwise be a limiting factor in the synthesis of zwittermicin A in the bacterial cell. Similar results have been obtained in other bacterial systems, in which the production of other metabolites by fermentation has been increased by improved routes of efflux from the cells of the product synthesized by the bacterial host. Regardless of whether the zmaR gene is, by itself, sufficient to increase the zwittermicin production by a particular bacterial strain, insofar as one seeks to create strains which have increased or enhanced zwittermicin A production capabilities, it would also be necessary to increase the efflux pump capabilities of those same cells, in order to ensure that one does not negatively select against high producers of zwittermicin A due to high levels of cytosolic zwittermicin A. Accordingly, *Bacillus cereus* cultures with enhanced levels of zmaR expression would be useful targets for directed mutagenesis to enhance levels of zwittermicin A biosynthesis.

The availability of the zmaR gene nucleotide sequence presented below also permits the ready use of information from that sequence to test new putative biocontrol strains for presence of the zmaR gene. Since most, if not all, native bacterial strains which produce zwittermicin A must also contain a gene encoding the resistance, it is logical to assume that those bacterial strains newly isolated from nature which harbor the zmaR gene would also natively have the ability to synthesize zwittermicin, and thus be effective as biocontrol agents. Using the modern techniques of molecular biology, it is well within the skill of ordinary practitioners in the art to create polymerase chain reaction (PCR) primers from the sequence information presented below, to probe the extracted DNA from any newly isolated bacterial strain for the presence of sequences which can be amplified using such probes. Such a PCR procedure is, in essence, an assay for the presence of the zmaR gene. Other techniques of selective DNA amplification are also well known to those of ordinary skill in the art. In addition, it is also possible to conduct DNA to DNA hybridization studies, using oligonucleotides created from the sequence information presented below, to probe DNA from such strains for the presence of hybridizing DNA sequences. Thus, a wide range of genetic tests are possible to assay for the presence of zmaR copies. As the results presented in the examples below will indicate, there is an extremely high correlation between those Bacillus isolates from around the world which contain copies of the zmaR gene, and those isolates which produce zwittermicin A and have biocontrol activity. Thus, the sequence information permits the rapid and efficient isolation and identification of novel biocontrol species from bacterial isolates in the Bacillus family.

In this regard, it should be noted that the native strain from which the zmaR gene has been isolated is classified as *B. cereus*. *B. cereus* is a member of a group of Bacillus strains including the species *B. mycoides*, *B. anthracis*, and *B. thuringiensis*. *B. mycoides* strains may be differentiated from *B. cereus* strains by the unique rhizoidal morphology of *B. mycoides*, and none of the strains described below which contain zmaR were classified as *B. mycoides* by this morphological analysis. It is believed that there are no *B. anthracis* strains in the strains described below, because *B. anthracis* is usually sensitive to ampicillin which probably prevented any strains from this species classification from being within the samples. However, differentiation between *B. cereus* and *B. thuringiensis* is difficult using standard methods. While current taxonomic recommendations have been followed in making the classifications below, it is perfectly reasonable to expect that there are native strains of *B. thuringiensis* which also contain the zmaR gene and produce zwittermicin. The data is consistent with the finding, made by others, that the effect of a molecule very much like zwittermicin A is produced by a *B. thuringienses* and potentiates or synergizes the activity of *B. thuringiensis* delta endotoxin protein (WO94/09630).

As the results below will indicate, the screening of new bacterial strains for zmaR gene presence is a powerful tool for locating biocontrol bacterial strains of the Bacillus family. Once a putative biocontrol strain is discovered, using the genetic techniques made possible by the sequence information presented below, it may be useful thereafter to conduct a plant protection assay, as described above, to verify the efficacy of the strain as a biocontrol agent. Such strains may also be useful for non-biocontrol purposes in addition, such as fermentation to produce zwittermicin A, which has independent utility as an antibiotic agent independent of its host organism.

The sequence information presented below is believed accurate. However, given the limitations and inherent occasional inaccuracies in current sequencing methods, it is possible that one or more single mis-identifications or omissions of a nucleotide might have occurred. However, most, if not all, of the nucleotide data is correct, and thus it is readily possible to design PCR oligonucleotide primers to amplify copies of the zmaR gene from *B. cereus* culture ATCC 53522. Also, the amino acid sequence presenced in SEQ ID: NO:2 is a deduced sequence from the longest open reading frame in SEQ ID: NO:1. Errors in nucleotide sequence may also cause corresponding errors in deduced amino acid sequence.

EXAMPLE 1

Plant Protection Assay of ATCC 53522 Using Alfalfa

The screening procedure disclosed above was repeated as an application of the plant protection assay to test the protective ability of ATCC 53522 with alfalfa. The cultivar of alfalfa used was Iroquois. The fungus used was Pmm. One gram of seeds was soaked in 18M sulfuric acid for ten minutes, washed in 2 l of sterile distilled water, placed in 10 ml of sterile distilled water, and shaken at 28° C. for 24 hours. Thereafter, the seed coats were removed with forceps, and the seedlings were planted in test tubes containing 5 ml of moist vermiculite. Three seedlings were planted in each test tube. After two days, each test tube was inoculated with 0.3 ml of a three day old culture of ATCC 53522 that had been grown in TSB to saturation. Thereafter, each tube was inoculated with $10^3$ zoospores of Pmm. The plants then were incubated at 24° C. with a 12 hour photo period for 7 days, whereupon the plants were evaluated for viability. All of the control seedlings were dead. Most of the seedlings that had been treated with ATCC 53522 had the appearance of normal seedlings that had not been exposed to Pmm.

EXAMPLE 2

Plant Protection Assay of ATCC 53522 with Soybeans

The procedure of Example 1 was repeated with soybeans of the variety McCall substituted for the alfalfa seeds and zoospores of *Phytophthora megasperma* f. sp. glycinea substituted for the zoospores of Pmm. Instead of being planted in test tubes, the soybean seeds were planted in 10 ml plastic cones having holes in the bottom, and the cones were placed in a pan of water. The seedlings were examined for protection two weeks after inoculation with the zoospores. Ten out of 10 controlled seedlings were killed by the fungus. All of the seedlings that had been treated with ATCC 53522 survived with healthy, white roots.

EXAMPLE 3

Field Test of ATCC 53522

Alfalfa seeds of the cultivar Iroquois were mixed in a suspension of ATCC 53522 in 1.5% methyl cellulose. The bacteria had been cultured on a TSA plate that had been incubated at 30° C. for three days, by which time the culture had sporulated. The culture then was scraped into 3 ml of the 1.5% methyl cellulose solution to provide the suspension of bacteria. One gram of alfalfa seeds was added to this suspension and was mixed thoroughly therewith. The seed then was spread on sterile petri plates and dried overnight in a laminar flow hood. The coated seeds were planted in circular plots 0.3 m in diameter at Marshfield, Wis. Owing to dry growing conditions, both emergence of plants and evidence of Pmm damping off were poor. Nevertheless, emergence in a control, untreated plot was 18% whereas in the plot planted with bacterium-treated seed, emergence was 30%. An additional plot was planted with seed that had been coated with a fungicide, metalaxyl, a conventional control agent for damping off. In that plot, emergence was 29%. Thus, it is apparent that ATCC 53522 can protect alfalfa in the field as effectively as does metalaxyl. Furthermore, symptoms of root rot became apparent in the control plot having untreated seeds as the growing season proceeded. No symptoms of root rot appeared in the plot planted with the seeds coated with ATCC 53522.

EXAMPLE 4

Plant Protection Assay of ATCC 53522 Toxin

The method of Example 1 was repeated with ATCC 53522 being replaced with a filtrate of a culture of that bacterium. The filtrate was prepared by centrifuging a two day old, saturated broth culture at 10,000 g for ten minutes and then filtering the resulting supernatant twice through 0.45μ filters. The filtrate was stored at −20° C. before being applied in the plant protection assay identically to the way the bacteria had been applied in the experiment reported as Example 1. The protective effect observed in treated alfalfa seedlings versus untreated seedlings was identical to that reported in Example 1. The filtrate used in this example contained *Bacillus cereus* antibiotic.

EXAMPLE 5

Spontaneous Mutants of ATCC 53522

Spontaneously developing antibiotic resistant mutants of ATCC 53522 were isolated by plating a culture derived from a colony of ATCC 53522 on media containing an antibiotic to which ATCC 53522 normally is sensitive. Several resistant colonies developed. They were each sampled with a sterile toothpick and replated on the antibiotic-containing media. The mutants were then tested in the plant protection assay by the procedure described in Example 1. Five mutants were developed that were resistant to rifampicin. A sixth mutant was developed that was resistant to neomycin. Each of the mutants protected alfalfa plants in the plant protection assay as applied in Example 1 as effectively as did ATCC 53522.

EXAMPLE 6

Induced Mutants of ATCC 53522

A culture of vegetatively growing cells of ATCC 53522 was prepared and diluted to a density of $10^8$ cells/ml. A quantity of this culture was treated by exposure to 1 μg/ml N-methyl-nitrosoguanidine for thirty minutes at room temperature. The cells then were washed with water and dilution plates were prepared on TSA. The treatment with N-methyl-nitrosoguanidine had killed 99% of the bacteria in the original culture. Thus, the remaining viable bacteria each had a high probability of containing at least one mutation. Of 500 such bacteria derived from independent colonies, 498 were able to protect alfalfa plants against Pmm when tested by the method of Example 1.

EXAMPLE 7

The assay procedure of Example 1 was again used to demonstrate that the plant protection activity resides with the *Bacillus cereus* antibiotic by testing filtrate fraction activity with the natural strain and antibiotic deficient mutants. Strain UW030 is such an antibiotic deficient mutant derived from *Bacillus cereus* ATCC 53522. The results of this procedure are demonstrated in Table 1 below.

TABLE 1

| | Plant Survival | |
|---|---|---|
| Treatment | Alfalfa | Tobacco |
| None | 0/18 | 0/12 |
| ATCC 53522 | 18/18 | 12/12 |
| ATCC 53522 filtrate | 18/18 | 12/12 |
| ATCC 53522 500–1000 fraction | 18/18 | 12/12 |
| UW030 | 0/18 | 2/12 |

TABLE 1-continued

| Treatment | Plant Survival | |
|---|---|---|
| | Alfalfa | Tobacco |
| UW030 filtrate | 0/18 | 1/12 |
| UW030 500–1000 fraction | 0/18 | 0/12 |

This demonstrates that the plant protecting activity is associated with the *Bacillus cereus* antibiotic independent of the bacteria, and that the activity is absent in antibiotic deficient mutants.

EXAMPLE 8

A *B. cereus* ATCC 53522 cultures were grown in half-strength trypticase soy broth (TSB). Then 1 liter, three-day old fully sporulated cultures were centrifuged to remove spores and the culture supernatant were adjusted to pH 7.0 with 2.0M $NaH_2PO_4$ and then applied to a column (2.2 cm×30.0 cm) containing Amberlite IRC-50 (Sigma). The column was washed with 5.0 mM $NH_4HPO_4/NH_3$ pH 7.0 and eluted with 1.0M $NH_3$ pH 11.2. The material in approximately 30 mls was collected from the column after the pH was raised above 10, dried in an evaporator, and quantified.

The active fractions were then purified by high voltage paper electrophoresis (HVPE) at pH 9.2. From the electrophoretograms, two spots were identified with the two antibiotics, zwittermicin A and antibiotic B. The spot for zwittermicin A had a relative mobility ($R_f$) of 0.30 compared to Orange G. The spot for antibiotic B had an $R_f$ of 0.032. These spots were eluted and subjected to HVPE at pH 1.7, at which the antibiotics exhibited mobilities similar to a di-cation ($R_f$=−1.042 for zwittermicin A and $R_f$=−0.909 for antibiotic B).

Separately, a panel of bacterial and pathogenic fungal strains were collected for use in an assay with purified zwittermicin A and antibiotic B to test antibiotic activity. The bacterial strains were all tested in Mueller-Hinton (MH) broth (Sigma) at pH 7.3 and MH broth buffered with 3-(n-morpholino) propanesulfonic acid (MOPs) to pH 8.0. The susceptibility testing of the Rhizobium and Lactobacillus strains were conducted in L-broth (Maniatis, 1982). Other strains requiring special treatment were the Rhodosprillum which was grown in MH broth to which 1 µg/ml of biotin was added, and the Clostridium which was grown in MH broth to which was added 20 µg/ml of sucrose.

The susceptibility testing of the fungal strains described below was conducted on potato dextrose agar (PDA) at pH 5.6 and PDA buffered with MOPs to pH 7.0.

For the bacterial susceptibility testing, the minimum inhibitory concentration (MICs) were determined by a broth dilution procedure. The inocula were prepared from fresh broth cultures and diluted to provide inoculum concentrations of approximately $5\times10^5$CFU/ml. Antibiotics were added in two-fold dilutions, ranging from 50 µg/ml to 400 µg/ml and each test tube contained 1 ml. The cultures were incubated at 28° C. with shaking for 24 h, (48 h for *Lactobacillus acidophilus, Streptomyces griseus, Rhizobium meliloti, Rhizobium tropici, Rhodobacter sphaeroides*, and *Rhodospirillum rubrum*). *Clostridium pasteurianum* was tested under anaerobic conditions by overlaying the culture with 3 ml of sterile mineral oil and then growing the culture for 4 days at room temperature. MICs were interpreted as the lowest antibiotic concentration that prevented visible growth. Bacteria with MICs of 50 µg/ml for zwittermicin A were retested at 0 to 50 µg/ml antibiotic in 10 µg increments. Minimal bactericidal concentrations (MBCs) were determined for each bacterial strain by spreading 0.1 ml from each test culture without visible growth onto Mueller-Hinton agar (Sigma Chemicals) plates. The plates were scored for bacterial growth after incubation at 28° C. for 24 to 48 h.

The zoosporic fungi were tested as follows: Zoospores of *Aphanomyces euteiches* ($2\times10^4$), *Phytophthora medicaginis* ($5\times10^4$), *Pythium aphanidermatum* ($1\times10^3$) and *Pythium torulosum* ($1\times10^3$) were spread onto PDA plates. A well was cut into the center of the agar with a sterilized cork borer. Purified antibiotic was pipetted into the well and the plates were incubated at room temperature for 48 h. Zones of inhibition were measured from the well to visible growth. MICs in this assay were the lowest antibiotic concentration that resulted in a zone of inhibition. *Candida utilus, Saccharomyes cerevisiae* and *Ustilaqo maydis* were tested by the same procedure and approximately $1\times10^4$ CFUs were spread on the PDA plates. *Venturia inaequalis* was tested by mixing $2\times10^5$ conidia into 25 ml of 50% PDA. The agar was vortexed briefly and then poured into a petri plate. A well was cut into the plate for the placement of antibiotic. The other fungi were tested for antibiotic susceptibility as follows: PDA plates were incubated with a plug of mycelia in the center of the plate. A well was cut into the agar 5 to 10 mm from the plug. Purified antibiotic (200) µg, was placed in the well and the plates were incubated at room temperature. Because of the variable growth rates of the test fungi, the plates were scored for growth after 2 to 6 days.

The data from the in vitro testing of antibiotic zwittermicin A and antibiotic B against bacteria is listed on Table 3 below while the results obtained from the testing against fungal pathogens is listed on Table 4 below. Also shown below, in Table 5, is an experiment conducted in which the combined activity of zwittermicin A and antibiotic B was evaluated against *E. coli*, at various combinations of each of the two antibiotics.

TABLE 2

In vitro activities of zwittermicin A and antibiotic B against bacteria

| | MIC (µg/ml)[a] | |
|---|---|---|
| Bacteria tested | ZmA | Ant B |
| *Agrobacterium tumefaciens* A759 | 40 | >400 |
| *Bacillus cereus* 569 | >400 | >400 |
| *Bacillus cereus* UW85 | >400 | >400 |
| *Bacillus cereus* BAR145 | >400 | >400 |
| *Bacillus subtilis* 168 | >400 | >400 |
| *Bacillus thuringiensis* 4A9 | >400 | >400 |
| *Bacillus thuringiensis* 4D6 | >400 | >400 |
| *Bradyrhizobium japonicum* USDA 110 | 100 | >400 |
| *Clostridium pasteurianum* 5002 | >400 | >400 |
| *Cytophaga johnsonae* 9408 | >400 | 300 |
| *Escherichia coli* K37 | 100 | >400 |
| *Erwinia carotovora* 8064 | 40 | >400 |
| *Erwinia herbicola* IRQ | >400 | >400 |
| *Erwinia herbicola* LS005 | 50 | 400 |

TABLE 2-continued In vitro activities of zwittermicin A
and antibiotic B against bacteria

| Bacteria tested | MIC (μg/ml)[a] | |
| --- | --- | --- |
| | ZmA | Ant B |
| Klebsiella pneumoniae 8030 | 200 | >400 |
| Lactobacillus acidophilus 4003 | 100 | >400 |
| Pseudomonas aeruginosa 9020 | >400 | >400 |
| Pseudomonas fluorescens 9023 | >400 | >400 |
| Rhizobium tropici CIAT 899 | 100 | >400 |
| Rhizobium meliloti 1021 | 50 | >400 |
| Rhodobacter sphaeroides 9502 | 50 | 400 |
| Rhodospirillum rubrum 9405 | 50 | >400 |
| Salmonella typhimurium LT2 | 100 | >400 |
| Staphylococcus aureus 3001 | 200 | 400 |
| Streptomyces griseus 6501 | 400 | >400 |
| Vibrio cholerae F115A | 400 | >400 |

TABLE 3

In vitro activities of zwittermicin A
and antibiotic B against various fungi

| Fungi tested | Disease incited | Inhibition[a] | |
| --- | --- | --- | --- |
| | | ZmA | Ant B |
| Alternaria alternata | Leaf blight on beet | + | +/− |
| Alternaria tagetica | Leaf and petal blight | + | +/− |
| Aphanomyces euteiches WI-98 | Seedling blight of alfalfa | + | + |
| Aspergillus flavus | Non-pathogenic | − | − |
| Botrytis cinerea | Molds and rots of stored fruits and vegetables | + | − |
| Candida utilus | Non-pathogenic | + | − |
| Colletotrichum phomoides | Anthracnose of tomato | +/− | − |
| Colletotrichum trifolii SMM | Anthracnose of alfalfa | + | − |
| Cytospora cineta | Branch canker of fruit trees | + | − |
| Drechslera poae | Leaf spot/foot rot of grasses | + | +/− |
| Epicoccum nigrum | Leaf spot of magnolia | + | − |
| Fusarium oxysporum f. sp. lycopersici | Vascular wilt of tomato | − | − |
| Fusarium sporotrichioides | Blight of barley and sunflower | + | +/− |
| Fusarium solani | Root rot of bean | + | − |
| Helminthosporium carbonum | Leaf spot and ear rot of corn | + | +/− |
| Helminthosporium sativum | Foot rot of grasses | + | +/− |
| Ophiostoma ulmi | Dutch elm disease | +/- | − |
| Phoma obscurans | Leaf spot of strawberry | + | +/− |
| Phytophthora medicaginis | Root rot of alfalfa | + | + |
| Pythium torulosum | Damping-off of tobacco | + | + |
| Pythium aphanidermatum | Root rot of vegetables | + | + |
| Rhizoctonia solani (AG1, AG4) | Root rot of fruits/ vegetables | + | − |
| Saccharomyces cerevisiae | Non-pathogenic | − | − |
| Sclerotinia homoecarpa | Dollar spot of turf | − | − |
| Sclerotinia sclerotiorum | Rots of most crops | + | − |
| Typhula incarnata | Snowmold of turf/grasses | − | − |
| Ustilago maydis | Smut of corn | + | + |
| Venturia inaequalis | Scab of apple | + | + |
| Verticillium dahliae | Wilt of potato | +/− | − |
| Verticillium albo-atrum | Wilt of alfalfa | +/− | − |

TABLE 4

Combined activity of zwittermicin A
and antibiotic B against E. coli

| | | Zwittermicin A (μg/ml) | | | | | |
| --- | --- | --- | --- | --- | --- | --- | --- |
| | | 0 | 10 | 15 | 20 | 25 | 30 | 40 |
| Antibiotic B (μg/ml) | 0 | +++ | + | + | + | + | + | − |
| | 50 | +++ | + | + | + | − | − | |
| | 100 | ++ | + | + | − | − | − | − |
| | 200 | ++ | − | − | − | − | − | |
| | 300 | ++ | − | − | − | − | − | |
| | 400 | − | − | − | − | − | − | |

Growth of E. coli strain K37 ranged from saturated cultures (+++) to no visible growth (−).

As the above data demonstrates, the antibiotics have broad spectrum activity against a variety of fungal pathogens and also have significant activity against many bacterial pathogens. In addition, from the E. coli study, it appears that the action of the antibiotics is synergistic and that they act in concert to achieve levels of inhibition that neither would achieve alone.

EXAMPLE 9

Construction of Gene Library and Identification of zmaR Gene

It had been inferred from previous work that resistance to zwittermicin A as a selectable phenotype that can be transferred to a bacterial strain that is otherwise sensitive to zwittermicin A. A bacterial strain sensitive to zwittermicin A, E. coli strain DH5α, was used as the host strain for a cosmid gene library prepared from the DNA of B. cereus strain UW85, ATCC 53522. For convenience in constructing the cosmid library, insert DNA was prepared from *B. cereus* strain UW101C, a derivative of UW85 that lacks a 14 Kb endogenous plasmid designated pBC85, Silo-Suh, *Appl. Environ. Microbiol.* 60:2023 (1994). The pBC85 deficient strain was used only since the plasmid pBC85 carries a "hot spot" for transposon insertion. The total genomic DNA was recovered from UW101C, and was partially digested with the restriction enzyme Sau3AI. Restriction fragments varying in size from 10 to 30 kb were recovered from an agarose gel. The DNA fragments were ligated into the BamHI site of the cosmid vector pLA2917 described by Allen and Hanson, *J. Bacteriol.*, 161:955–962 (1985). The cosmid vector pLA2917 carries tetracycline and kanamycin resistance markers, and the insertion site disrupted the kanamycin resistance marker on the cosmid vector. The ligation mixture was packaged in lambda phage heads using a commercially available DNA packaging kit (Borehringer Mannhelm) and transfected into *E. coli* strain DHSα. A total of 350 tetracycline resistance and kanamycin sensitive transfected colonies were obtained. One batch of 250 transfectants, and a second batch of 100 transfectants, were pooled and the pools were stored at −70° C. until ready for use.

The cosmid library was then screened to identify cosmids that conferred zwittermicin A resistance. The procedure was conducted by taking cells from the culture of pooled transfectants and spreading them on Mueller-Hinton agar, pH 8.0 (Difco Laboratories) into three evenly spaced wells cut in an agar plate, into which was also introduced 100 μg of zwittermicin A, after which the plates were incubated at 28° C. for 24 hours. Those colonies that grew up within a 15 mm zone of inhibition of growth around the cells were defined to be zwittermicin A resistant, and the colonies arose at a frequency of approximately $1 \times 10^{-2}$. The 118 zwittermicin A resistant colonies thus obtained were stored on Luria agar plates amended with tetracycline at 20 µg/ml. Cosmid DNA was then prepared from ten of the zwittermicin A resistant isolates, and digested with the restriction enzymes EcoRI and HinDIII, and the fragments were separated by agarose gel electrophoresis. From these gels, it was estimated that the size of the cosmid inserts was approximately 19 kb. Two distinct banding patterns, indicating bands of common size, were observed and Southern blots verified that there were two cosmid inserts with overlapping DNA, those inserts then being designated pZmR6 and pZmR7. When these cosmids were transferred into other colonies of DH5α, zwittermicin A resistance was also transferred with the cosmids, and when the cosmids were lost, resistance to zwittermicin A was also lost by the transfected colonies.

Figure 2:
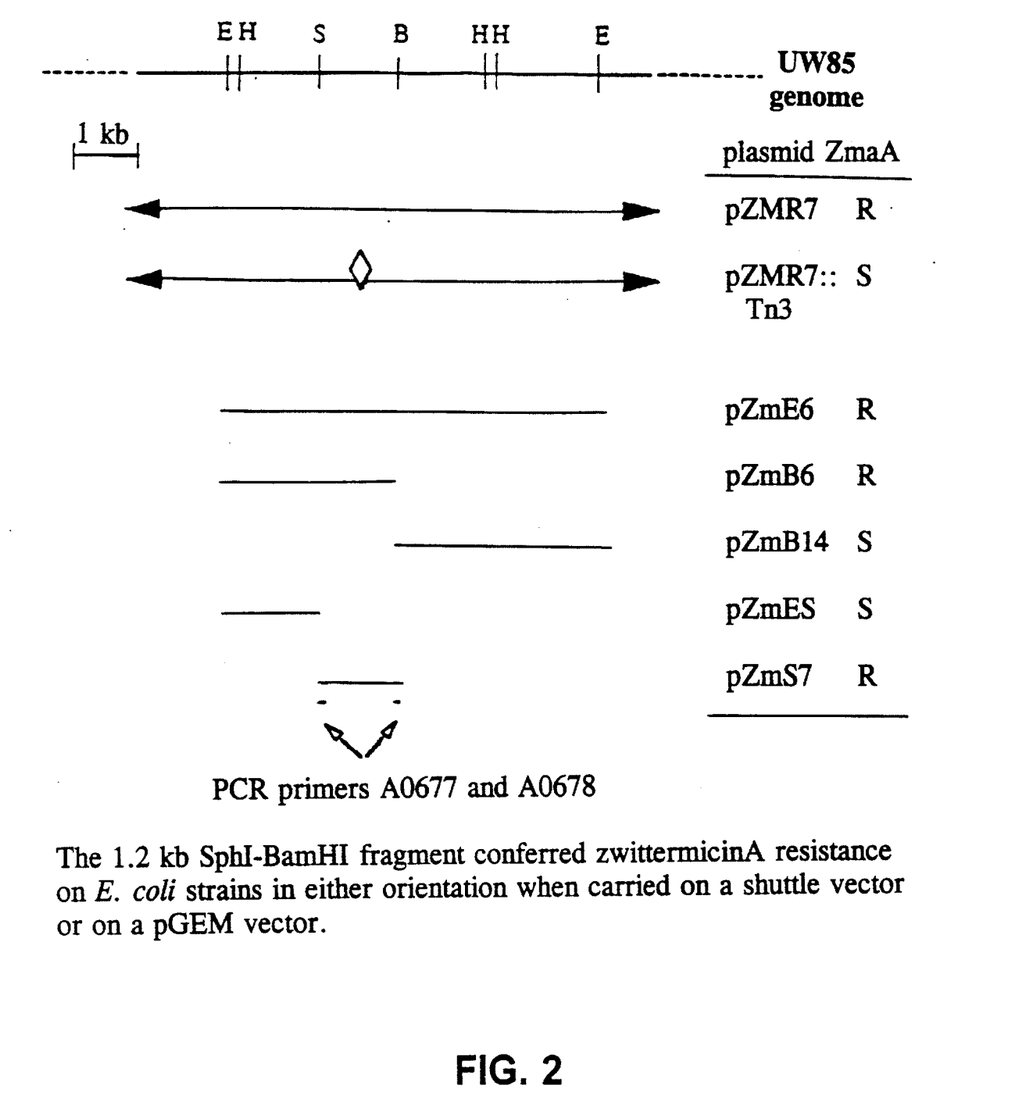
FIG. 2 is a schematic illustration of the genetic fragments obtained from the *B. cereus* ATCC 53522 genome during the characterization of the zmaR gene.

In order to locate more precisely the zmaR gene within the cosmids, cosmid pZmR7 was mutagenized with Tn3, which carries a kanamycin resistance marker. The mutants thus created were screened for sensitivity to zwittermicin A in a radial streak assay, in which 50 µg of an aqueous solution of zwittermicin A is applied to a filter disc placed in the center of a Mueller-Hinton (pH 8.0) plate, and test cultures are streaked from near the disc radially outward to the edge of the agar plate with a sterile stick. One zmaR::Tn3 mutant was identified out of 160 colonies screened. By restriction digestion analysis, the Tn3 insertion was mapped to a 5 kb EcoRI fragment of the pZmR7 cosmid. Shown in FIG. 2 is a schematic representation of the location of EcoRI fragment and the Tn3 insert mapped onto pZmR7.

The 5 kb EcoRI fragment was then subcloned into the unique EcoRI site within the multiple cloning site of the shuttle vector pHT304, as described by Arantes and Lereclus, Gene 108:115–119 (1991). The recombinant plasmid was designated pZmE6R. This plasmid was found to confer zwittermicin resistance on naive colonies of E. coli DH5α. As is generally illustrated in FIG. 2, additional digestion with restriction enzymes was conducted, to more localize the sequence which conferred the zwittermicin A resistance. A 1.2 kb SphI-BamHI fragment, which corresponded to the site of the Tn3 Lnsertion in pZmR7, was found to be sufficient to confer zwittermicin A resistance on naive colonies of E. coli DH5α, in either orientation, when cloned into the shuttle vector pHT304 or, in the alternative, in the sequencing vector pGEM. This result confirmed that the zmaR gene was Located within the 1.2 kb fragment, and confirmed that all regulatory and protein coding information necessary to confer zwittermicin A resistance was contained within that fragment. The information in SEQ ID:1.

EXAMPLE 10

PCR Amplification of zmaR

Using plasmid pZmG6 (the 1.2 kb BamHI-SphI fragment cloned into the sequencing vector pGEM) as a template, and the universal forward and reverse pUC/M13 primers, sufficient sequence information was generated to design specific primers for use in polymerase chain reaction (PCR) amplification of zmaR, based on the sequence information of about 150 bases from each end of the fragments. This is generally illustrated in FIG. 1. Two primers separated by approximately 1 kb were designed from the DNA sequence. The primers were designated and constructed as follows:
AO677 5' TAAAGCTCGTCCCTCTTCAG 3'SEQ ID NO:3

AO678 5' ATGTGCACTTGTATGGGCAG 3' SEQ ID NO:4

The position of these primers on the pZmR7 insert is illustrated in FIG. 1.

A PCR method was used to amplify the coding sequence. This same PCR method may be used for amplification of zmaR sequences from other hosts as well. The template DNA for PCR was isolated using a rapid cell lysis method. The test strain was inoculated into 1 ml of brain heart infusion medium and was then incubated at 28° C. with shaking for 16 hours. A portion of the culture (approximately 600 µl) was transferred to a 1.5 ml microfuge tube and the cells were pelleted by centrifugation (14,000×gravity for 10 minutes). The pellet was resuspended in 300 µl of sterile water and the cells were heated in a 95° C. water bath for 15 minutes. Cell debris was removed by centrifugation (14,000×gravity for 5 minutes) and the DNA solution was transferred to a new tube.

The template DNA was then amplified by a PCR reaction in a 50 µl reaction mixture containing 10 mM Tris pH 8.3, 50 mM KCl, 1.5 mM $MgCl_2$, 0.001% gelatin (Perkin Elmer Cetus 10×buffer), 200 µM of each dNTP, 1.25 U native Taq polymerase (Perkin Elmer Cetus), 10–20 ng of template DNA, and 1 µM of each primer. The reaction was overlaid with 30 µl mineral oil (Sigma). The PCR reaction was carried out in a Stratagene thermocycler using the following schedule: 1 cycle at 94° C. for 5 minutes; 45 cycles at 94° C. for 1 minute, 56° C. for 1 minute, and 72° C. for 2 minutes; and a final extension of 72° C. for 5 minutes. A 15 µl sample of the PCR reaction product was subjected to electrophoresis in a gel containing 0.75% Synergel/0.5% Seakem agarose in TBE (Tris barate EDTA electrophoresis buffer). Bands were visualized by ethidium bromide staining. A series of three bands sized to be 1.2 kb, 1.0 kb, and 0.3 kb was characteristic of the amplification products of ATCC 53522 and was similarly characteristic of reaction products obtained using other plasmids carrying the zmaR gene as the template.

EXAMPLE 11

Testing of New Strains for zmaR gene

The sequence information obtained above was then used to screen a collection of Bacillus isolates obtained from around the world, that had also been tested for zwittermicin A production. Cultures of each of the bacteria were isolated by placing 1 g of root or soil section from alfalfa or soybean into 9 ml of sterile water, sonicating for 30 seconds to release the bacteria into the water, and plating serial 10-fold dilutions on 1/10th strength trypticase soy agar (3 g/l, Becton Dickinson Microbiology Systems). After 1 to 3 days incubation at 28° C., colonies with the morphology characteristics of B. cereus (i.e. flat, broad, white, rough surface, irregular edges, and 1–3 mm in diameter) were streaked for isolated colonies. The medium for the cultivation of the isolated colonies was supplemented with polymyxin (25 µg/ml), cycloheximide (100 µg/ml), and ampicillin (50 µg/ml) during the initial plating and all subsequent streak plating, as a partial selection for strains which were B. cereus. All isolates were selected for hemolysis of blood on half-strength trypticase soy agar containing 5% sheep red blood cells, a test which is also diagnostic of B. cereus, and those that were nonhemolytic were removed from the collection. Isolates which passed the above screening criteria were stored on half-strength trypticase soy agar slants.

Forty-seven of the isolates were analyzed by fatty acid profile analysis by commercial laboratories. All of the isolates were classified as members of the B. cereus group, which includes the species B. mycoides, B. anthracis and B. thurinqiensis. Because of the rhizoidal morphology of B. mycoides strains, strains of this species were believed eliminated from the collection by morphological classification. The strains of B. anthracis are normally not hemolytic and are usually sensitive to ampicillin, and it was therefore believed that there were no B. anthracis cultures in the collection. Differentiation between B. cereus and B. thuringiensis cultures was uncertain but was conducted in accordance with current taxonomic recommendations as set forth by Lysenko, *J. Invertebr. Pathol.* 42:295–298 (1983) and Priest, "Systematics and Ecology of Bacillus" in *Bacillus Subtillis and Other Gram-Positive Bacteria*, Sonenshein et al. Eds., American Society for Microbiology, Washington, DC (1993). All isolates were considered to be B. cereus by this classification.

The isolates of B. cereus were tested for zwittermicin A production by methods similar to that described above. Triplicate cultures of the candidate cultures were grown with shaking at 28° C. for 4 or 5 days until they contained predominantly released spores. Bacteria were removed from the remainder of the culture by centrifugation and a supernatant was adjusted to pH 6.8 to 7.0 with 1M $NH_4H_2PO_4$. A known volume of supernatant (7 to 10 ml) was passed over a CM-Sep-Pak cartridge (Millipore) pre-equilibrated with 10 ml of 5 mM ammonium phosphate buffer, pH 7.0. The CM-Sep-Pak cartridge was washed with 10 ml of the same buffer and zwittermicin A was eluted with 1.5 ml of 1M $NH_4OH$. The eluant was dried under vacuum and the resulting residue was resuspended in water at a rate of about 1.5 µl/ml of original supernatant. The antibiotic was quantified by end-point dilution assay conducted by the method described by Silo-Suh et al., *Appl. Environ. Microbiol.* 60:2023–2030 (1994). Briefly, dilutions of the partially purified zwittermicin A and dilutions of known amount of authentic zwittermicin A were subjected to high-voltage paper electrophoresis. Antibiotics were detected on the electrophoretograms by silver staining. The amount of zwittermicin A in samples was calculated by comparison with dilutions of spiked authentic zwittermicin A used as the relative standard.

Genomic DNA was prepared from 38 strains from the culture collection of B. cereus cultures described above. The cultures had been analyzed by the zwittermicin A assay method to be classified as either zwittermicin A producers or zwittermicin A non-producers. All of the template DNA was then used to test for the presence, by PCR reaction, of the zmaR gene therein. The results are summarized in Table 5 below. All zwittermicin A producers, except for one (LS2-12), carried the gene zmaR as shown by the presence of the characteristic amplified DNA though some strains did not have a detectable 300 bp band. Several non-producers also tested positive by PCR analysis for the zmaR gene, but those producers were sensitive to zwittermicin A indicating that the gene product was ineffective or non-expressed. These results demonstrated the ability of the PCR analysis for the presence of the zmaR gene to identify cultures which were producers of zwittermicin A.

To verify that this test could be used to screen novel isolates from the soil, *Bacillus cereus*-like isolates were obtained from soil samples from Madison, Wisconsin, USA and from Zamorano, Honduras using the method described above. Template genomic DNA was prepared from 56 isolates obtained from Wisconsin soil and 59 isolates from Honduras soil and those template samples were used in a PCR amplification reaction for the zmaR gene using the templates described above. Of those isolates, 32 of the isolates (16 from each site) produced the three characteristic amplification products analogous to those produced by ATCC 53522 although in some strains the 300 bp fragment was not detected. No amplification products were detected in any of the other isolates. Twelve of the isolates that tested positive and 12 of the isolates that tested negative for presence of the zmaR gene by PCR analysis were then subsequently tested for zwittermicin A production by the methods described above. Only isolates that carried the zmaR gene, determined by PCR analysis, were also found to produce zwittermicin A. These results are set forth in Table 6 below.

TABLE 5

*Bacillus cereus* isolates that produce zwittermicin A carry the zmaR gene

| Strain | Origin | Zwittermicin A Production | Zwittermicin A Resistance | zmaR gene |
|---|---|---|---|---|
| UW85 | USA | + | R | + |
| ALF 19 | USA | + | R | + |
| ALF 52 | USA | + | R | + |
| ALF 95 | USA | + | R | + |
| ALF 133 | USA | + | R | + |
| ALF 166 | USA | + | R | + |
| ARL 8 | USA | + | R | + |
| AS 4-12 | USA | + | R | + |
| DGA 37 | Australia | + | R | + |
| DGA 84 | Australia | + | R | + |
| HS 23-11 | USA | + | R | + |
| LN 100 | Netherlands | + | R | + |
| LS 2-12 | USA | + | R | + |
| Sny 44 | Panama | + | R | + |
| SOY 130 | USA | + | R | + |
| VGA 577 | Honduras | + | R | + |
| WS 8-8 | USA | + | R | + |
| WS 10-15 | USA | + | R | + |
| Bt HD1 | ATCC | + | R | + |
| Bt 4F1 | ATCC | + | R | + |
| Bt 4S2 | ATCC | + | R | + |
| Bc 569 | ATCC | – | R | + |
| Bt 4E1 | ATCC | – | S | –* |
| ALF 10 | USA | – | S | – |
| ALF 93 | USA | – | S | + |
| ALF 85 | USA | – | S | + |
| ALF 98 | USA | – | S | + |
| ALF 99 | USA | – | S | + |
| ALF 109 | USA | – | S | + |
| ALF 137 | USA | – | S | – |
| ALF 144 | USA | – | S | + |
| ALF 173 | USA | – | S | – |
| Bar 145 | Panama | – | S | – |
| LN 74 | Netherlands | – | S | – |
| Lutz 58 | Panama | – | S | – |
| Sny 73 | Panama | – | S | – |
| Vga 562 | Honduras | – | S | – |
| WS 4-12 | USA | – | S | – |

[a]Resistance of strains to zwittermicin A (300 ug) as determined by the radial streak assay. R, resistant, no zone of inhibition. S, sensitive, zones from 3 mm to 10 mm.
[b]PCR products from the resistance gene primers AO677 and AO678.
+ indicates bands at 1200 bp, 1000 bp and 300 bp;
– indicates no bands.
*One band at 700 bp.

TABLE 6

Screening *Bacillus cereus* isolates for the zmaR gene identifies zwittermicin A producers

| Strain | zmaR Gene 1.2, 1.0 kb PCR product | 0.3 kb PCR product | Zwittermicin A production |
|---|---|---|---|
| W6 | + | + | + |
| W8 | − | − | − |
| W9 | + | − | + |
| W10 | − | − | − |
| W21 | + | − | −? |
| W23 | − | − | − |
| W28 | + | − | + |
| W31 | − | − | − |
| W35 | + | + | + |
| W38 | − | − | − |
| W48 | − | − | − |
| W50 | + | + | + |
| Z7 | − | − | − |
| Z8 | + | + | + |
| Z12 | − | − | − |
| Z33 | + | + | + |
| Z39 | + | − | ? |
| Z42 | + | + | + |
| Z49 | − | − | − |
| Z53 | − | − | − |
| Z54 | + | − | + |
| Z66 | − | − | − |
| UW85 | + | + | + |

EXAMPLE 12

Transformation of cultures to overproduce zwittermicin

The availability of the zmaR gene make possible engineering Bacillus strains which produce zwittermicin to enhance their expression of the zmaR. By doing this, the bacteria will be free to produce greater quantities of zwittermicin, the synthesis of which is normally limited by biochemical feedback mechanisms in the cell response to zwittermicin concentration.

The 5 kb EcoRI fragment carrying the zmaR gene has be introduced into the shuttle vectors pHT304, pHT315 and pHT370 which vectors include 5, 15 and 70 copies of the fragment respectively. These vectors can be used to deliver the fragment, including the zmaR gene, into a Bacillus host. Alternatively, the coding sequence for the zmaR gene can be ligated into a vector under the regulation of a well characterized promoter to increase expression under controlled conditions. *B. cereus* cultures, such as UW85 ATCC 53522, engineered in this manner will secrete greater amounts of free zwittermicin into their host medium as the enhanced activity of the efflux pump removes zwittermicin from the cells.

What is claimed is:

1. A novel DNA construction isolated from its native host comprising a nucleotide sequence which can be expressed to encode a *Bacillus cereus* protein which, when present in a bacterial host cell, confers resistance in the host cell to the antibiotic zwittermicin A.

2. A DNA sequence isolated from any host comprising a nucleotide sequence encoding a protein having the amino acid sequence of SEQ ID NO: 2.

3. A DNA construction isolated from *Bacillus cereus* comprising the DNA sequence of SEQ ID NO: 1.

4. A novel DNA construction isolated from its native host comprising the zmaR gene from *Bacillus cereus*.

5. An isolated DNA sequence comprising a nucleotide sequence encoding a protein having the amino acid sequence of SEQ ID NO: 2.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1229 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Bacillus cereus
        ( B ) STRAIN: UW85 (ATCC 53522)

( i x ) FEATURE:
        ( A ) NAME/KEY: CDS
        ( B ) LOCATION: 47..1174

( i x ) FEATURE:
        ( A ) NAME/KEY: primer_bind
        ( B ) LOCATION: 193..212
        ( C ) IDENTIFICATION METHOD: experimental
        ( D ) OTHER INFORMATION: /evidence= EXPERIMENTAL
            / standard_name= "Binding site for primer AO678"

( i x ) FEATURE:
        ( A ) NAME/KEY: primer_bind
        ( B ) LOCATION: complement (1125..1144)
        ( C ) IDENTIFICATION METHOD: experimental
        ( D ) OTHER INFORMATION: /evidence= EXPERIMENTAL
            / standard_name= "Binding site for primer AO677"

( x i ) SEQUENCE DESCRIPTION: SEQ ID NO:1:

```
TGCATGCACT  TCGCACTTGT  TCTCAAAAGG  GAGGACTTTT  AAGAAT ATG ATT TAT           55
```

|   |   |   |   |   |   |   |   |   |   |   |   |   |   |   |   |
|---|---|---|---|---|---|---|---|---|---|---|---|---|---|---|---|
|   |   |   |   |   |   |   |   |   |   |   |   | Met | Ile | Tyr |   |
|   |   |   |   |   |   |   |   |   |   |   |   | 1   |     |     |   |
| GAA | TTG | GTA | AAA | GAA | AAG | GAT | GCA | TTC | AAA | CAA | ATA | TCT | CCA | CTT | CTC | 103 |
| Glu | Leu | Val | Lys | Glu | Lys | Asp | Ala | Phe | Lys | Gln | Ile | Ser | Pro | Leu | Leu |   |
|     | 5   |     |     |     | 10  |     |     |     |     | 15  |     |     |     |     |     |   |
| GTT | GAT | TAT | AAG | AAC | CAT | CCA | ATA | CTG | AAC | GGT | ATA | GCT | CAT | GGT | TAC | 151 |
| Val | Asp | Tyr | Lys | Asn | His | Pro | Ile | Leu | Asn | Gly | Ile | Ala | His | Gly | Tyr |   |
| 20  |     |     |     |     | 25  |     |     |     |     | 30  |     |     |     |     | 35  |   |
| AAT | AAG | GGA | CAT | ATT | TAT | GTG | GAT | AAT | CCT | AAT | AAC | CCT | AGA | TGT | GCA | 199 |
| Asn | Lys | Gly | His | Ile | Tyr | Val | Asp | Asn | Pro | Asn | Asn | Pro | Arg | Cys | Ala |   |
|     |     |     |     | 40  |     |     |     |     | 45  |     |     |     |     | 50  |     |   |
| CTT | GTA | TGG | GCA | GAA | CAA | GAA | ATT | TTT | TAT | TTA | TTA | GGT | GAT | CCT | ACA | 247 |
| Leu | Val | Trp | Ala | Glu | Gln | Glu | Ile | Phe | Tyr | Leu | Leu | Gly | Asp | Pro | Thr |   |
|     |     |     | 55  |     |     |     |     | 60  |     |     |     |     | 65  |     |     |   |
| AGT | AAT | TTT | GTT | TCA | AGT | CTA | CCA | ACT | TTT | ATT | AAA | GAA | GTA | ATT | GCA | 295 |
| Ser | Asn | Phe | Val | Ser | Ser | Leu | Pro | Thr | Phe | Ile | Lys | Glu | Val | Ile | Ala |   |
|     |     | 70  |     |     |     |     | 75  |     |     |     |     | 80  |     |     |     |   |
| CCT | GAG | GCT | GAG | CAG | ATA | GGG | GAT | GAC | TTT | TTT | CAG | GTT | GAA | TTA | TTA | 343 |
| Pro | Glu | Ala | Glu | Gln | Ile | Gly | Asp | Asp | Phe | Phe | Gln | Val | Glu | Leu | Leu |   |
|     | 85  |     |     |     |     | 90  |     |     |     |     | 95  |     |     |     |     |   |
| CCT | GAA | TCA | AAA | TGG | AAA | CAG | GTT | GTC | GAG | GAA | CAA | TTG | CAA | ATG | TTT | 391 |
| Pro | Glu | Ser | Lys | Trp | Lys | Gln | Val | Val | Glu | Glu | Gln | Leu | Gln | Met | Phe |   |
| 100 |     |     |     |     | 105 |     |     |     |     | 110 |     |     |     |     | 115 |   |
| ATT | CCT | AAA | CCT | TAC | ACT | CGA | GTA | ACA | TTT | ACT | TTT | GAT | CCG | GAG | TCT | 439 |
| Ile | Pro | Lys | Pro | Tyr | Thr | Arg | Val | Thr | Phe | Thr | Phe | Asp | Pro | Glu | Ser |   |
|     |     |     |     | 120 |     |     |     |     | 125 |     |     |     |     | 130 |     |   |
| TAT | AAT | AAG | TTA | TCT | AAA | CCT | AAT | ATG | CCT | GAA | GAG | GTA | ACG | GTG | GAA | 487 |
| Tyr | Asn | Lys | Leu | Ser | Lys | Pro | Asn | Met | Pro | Glu | Glu | Val | Thr | Val | Glu |   |
|     |     |     | 135 |     |     |     |     | 140 |     |     |     |     | 145 |     |     |   |
| CGT | ATT | ACA | ATC | GAC | ATG | CTA | TCA | GAT | AAA | AAG | TTC | GCA | ATG | GTA | CGG | 535 |
| Arg | Ile | Thr | Ile | Asp | Met | Leu | Ser | Asp | Lys | Lys | Phe | Ala | Met | Val | Arg |   |
|     |     | 150 |     |     |     |     | 155 |     |     |     |     | 160 |     |     |     |   |
| GAT | GAT | ATT | GTT | GAT | TTT | TGG | GAG | TCA | ACT | CAG | GAT | TTC | ATC | CAA | AAT | 583 |
| Asp | Asp | Ile | Val | Asp | Phe | Trp | Glu | Ser | Thr | Gln | Asp | Phe | Ile | Gln | Asn |   |
|     | 165 |     |     |     |     | 170 |     |     |     |     | 175 |     |     |     |     |   |
| GGA | TTT | GGT | TAT | GTA | GTA | ATG | GTA | CAT | GAA | CAA | GTT | GTA | ACT | AGT | TGC | 631 |
| Gly | Phe | Gly | Tyr | Val | Val | Met | Val | His | Glu | Gln | Val | Val | Thr | Ser | Cys |   |
| 180 |     |     |     |     | 185 |     |     |     |     | 190 |     |     |     |     | 195 |   |
| TTA | TCG | GTT | TTT | GCA | ACA | GAT | ACT | GAT | GTG | GAA | ATT | GGA | ATT | AAT | ACT | 679 |
| Leu | Ser | Val | Phe | Ala | Thr | Asp | Thr | Asp | Val | Glu | Ile | Gly | Ile | Asn | Thr |   |
|     |     |     |     | 200 |     |     |     |     | 205 |     |     |     |     | 210 |     |   |
| TAT | GAT | TTA | TTC | CAG | CGA | GGT | AAA | GGG | TAT | GCT | TGG | TTG | GCT | GCA | AGA | 727 |
| Tyr | Asp | Leu | Phe | Gln | Arg | Gly | Lys | Gly | Tyr | Ala | Trp | Leu | Ala | Ala | Arg |   |
|     |     |     | 215 |     |     |     |     | 220 |     |     |     |     | 225 |     |     |   |
| GCA | TTC | TTG | GAT | GAC | TGT | TTA | AAA | CAA | GGA | AGA | ACA | CCA | CAT | TGG | AAG | 775 |
| Ala | Phe | Leu | Asp | Asp | Cys | Leu | Lys | Gln | Gly | Arg | Thr | Pro | His | Trp | Lys |   |
|     |     | 230 |     |     |     |     | 235 |     |     |     |     | 240 |     |     |     |   |
| ACG | GAG | GAT | TTT | CGT | ATT | CCA | TCT | ATT | AAA | CTA | GCG | GGA | AAA | GTT | GGA | 823 |
| Thr | Glu | Asp | Phe | Arg | Ile | Pro | Ser | Ile | Lys | Leu | Ala | Gly | Lys | Val | Gly |   |
|     | 245 |     |     |     |     | 250 |     |     |     |     | 255 |     |     |     |     |   |
| TTC | ACA | AAT | CTT | CAA | ACC | TAT | ACA | GCT | TAT | GTG | TTT | CCT | TAT | AAC | GAA | 871 |
| Phe | Thr | Asn | Leu | Gln | Thr | Tyr | Thr | Ala | Tyr | Val | Phe | Pro | Tyr | Asn | Glu |   |
| 260 |     |     |     |     | 265 |     |     |     |     | 270 |     |     |     |     | 275 |   |
| TTA | GAT | AAT | TTC | ATT | TTT | ACC | GCG | TAC | CAT | CAA | TTA | AGA | TAC | TAT | TCA | 919 |
| Leu | Asp | Asn | Phe | Ile | Phe | Thr | Ala | Tyr | His | Gln | Leu | Arg | Tyr | Tyr | Ser |   |
|     |     |     |     | 280 |     |     |     |     | 285 |     |     |     |     | 290 |     |   |
| AAT | TTT | AAT | AAA | GCT | AGT | GAG | TTT | GTA | CAA | AAA | GCT | CGT | ACT | ATA | GGA | 967 |
| Asn | Phe | Asn | Lys | Ala | Ser | Glu | Phe | Val | Gln | Lys | Ala | Arg | Thr | Ile | Gly |   |
|     |     |     | 295 |     |     |     |     | 300 |     |     |     |     | 305 |     |     |   |
| GAT | TTA | AAT | GCA | TGG | CAT | CAC | TTT | TTA | CTT | TCA | TGT | GGT | TAT | TCA | TTA | 1015 |

```
Asp  Leu  Asn  Ala  Trp  His  His  Phe  Leu  Leu  Ser  Cys  Gly  Tyr  Ser  Leu
          310                 315                      320

ATT  GAT  AGA  ATC  GAT  CTT  TCG  TTA  AAG  CAT  ATG  AAT  CTT  GCA  CTA  GAT      1063
Ile  Asp  Arg  Ile  Asp  Leu  Ser  Leu  Lys  His  Met  Asn  Leu  Ala  Leu  Asp
          325                 330                      335

CTA  GGA  TGG  AAT  GAT  GTA  TCA  GAT  ATT  CGC  TAT  GTA  GTT  GAT  TTA  GTG      1111
Leu  Gly  Trp  Asn  Asp  Val  Ser  Asp  Ile  Arg  Tyr  Val  Val  Asp  Leu  Val
340                      345                 350                           355

AAT  TTA  AGA  AAA  ACT  GAA  GAG  GGA  CGA  GCT  TTA  TTA  GAT  AGA  GTT  GAA      1159
Asn  Leu  Arg  Lys  Thr  Glu  Glu  Gly  Arg  Ala  Leu  Leu  Asp  Arg  Val  Glu
               360                      365                      370

GAT  AGC  TTA  AGA  TGA  AAATAAGGGA GATAAAAAGA TGAATATTGT ATTTATGTTT                 1214
Asp  Ser  Leu  Arg   *
               375

CCTGGCGTAG GATCC                                                                     1229
```

( 2 ) INFORMATION FOR SEQ ID NO:2:

( i ) SEQUENCE CHARACTERISTICS:
    ( A ) LENGTH: 375 amino acids
    ( B ) TYPE: amino acid
    ( D ) TOPOLOGY: linear   ( i i ) MOLECULE TYPE: protein   ( x i ) SEQUENCE DESCRIPTION: SEQ ID NO:2:

```
Met  Ile  Tyr  Glu  Leu  Val  Lys  Glu  Lys  Asp  Ala  Phe  Lys  Gln  Ile  Ser
 1              5                       10                       15

Pro  Leu  Leu  Val  Asp  Tyr  Lys  Asn  His  Pro  Ile  Leu  Asn  Gly  Ile  Ala
               20                  25                       30

His  Gly  Tyr  Asn  Lys  Gly  His  Ile  Tyr  Val  Asp  Asn  Pro  Asn  Asn  Pro
                35                  40                  45

Arg  Cys  Ala  Leu  Val  Trp  Ala  Glu  Gln  Glu  Ile  Phe  Tyr  Leu  Leu  Gly
      50                  55                       60

Asp  Pro  Thr  Ser  Asn  Phe  Val  Ser  Ser  Leu  Pro  Thr  Phe  Ile  Lys  Glu
65                       70                       75                       80

Val  Ile  Ala  Pro  Glu  Ala  Glu  Gln  Ile  Gly  Asp  Asp  Phe  Phe  Gln  Val
                85                       90                       95

Glu  Leu  Leu  Pro  Glu  Ser  Lys  Trp  Lys  Gln  Val  Val  Glu  Glu  Gln  Leu
               100                 105                      110

Gln  Met  Phe  Ile  Pro  Lys  Pro  Tyr  Thr  Arg  Val  Thr  Phe  Thr  Phe  Asp
          115                 120                      125

Pro  Glu  Ser  Tyr  Asn  Lys  Leu  Ser  Lys  Pro  Asn  Met  Pro  Glu  Glu  Val
     130                 135                      140

Thr  Val  Glu  Arg  Ile  Thr  Ile  Asp  Met  Leu  Ser  Asp  Lys  Lys  Phe  Ala
145                 150                      155                      160

Met  Val  Arg  Asp  Asp  Ile  Val  Asp  Phe  Trp  Glu  Ser  Thr  Gln  Asp  Phe
               165                      170                      175

Ile  Gln  Asn  Gly  Phe  Gly  Tyr  Val  Val  Met  Val  His  Glu  Gln  Val  Val
               180                      185                      190

Thr  Ser  Cys  Leu  Ser  Val  Phe  Ala  Thr  Asp  Thr  Asp  Val  Glu  Ile  Gly
          195                      200                 205

Ile  Asn  Thr  Tyr  Asp  Leu  Phe  Gln  Arg  Gly  Lys  Gly  Tyr  Ala  Trp  Leu
     210                      215                 220

Ala  Ala  Arg  Ala  Phe  Leu  Asp  Asp  Cys  Leu  Lys  Gln  Gly  Arg  Thr  Pro
225                      230                 235                      240

His  Trp  Lys  Thr  Glu  Asp  Phe  Arg  Ile  Pro  Ser  Ile  Lys  Leu  Ala  Gly
               245                      250                      255
```

| | | | | | | | | | | | | | | |
|---|---|---|---|---|---|---|---|---|---|---|---|---|---|---|
| Lys | Val | Gly | Phe 260 | Thr | Asn | Leu | Gln | Thr 265 | Tyr | Thr | Ala | Tyr | Val 270 | Phe | Pro |
| Tyr | Asn | Glu 275 | Leu | Asp | Asn | Phe | Ile 280 | Phe | Thr | Ala | Tyr | His 285 | Gln | Leu | Arg |
| Tyr | Tyr 290 | Ser | Asn | Phe | Asn | Lys 295 | Ala | Ser | Glu | Phe | Val 300 | Gln | Lys | Ala | Arg |
| Thr 305 | Ile | Gly | Asp | Leu | Asn 310 | Ala | Trp | His | His | Phe 315 | Leu | Leu | Ser | Cys | Gly 320 |
| Tyr | Ser | Leu | Ile | Asp 325 | Arg | Ile | Asp | Leu | Ser 330 | Leu | Lys | His | Met | Asn 335 | Leu |
| Ala | Leu | Asp | Leu 340 | Gly | Trp | Asn | Asp | Val 345 | Ser | Asp | Ile | Arg | Tyr 350 | Val | Val |
| Asp | Leu | Val 355 | Asn | Leu | Arg | Lys | Thr 360 | Glu | Glu | Gly | Arg | Ala 365 | Leu | Leu | Asp |
| Arg | Val 370 | Glu | Asp | Ser | Leu | Arg 375 | | | | | | | | | |

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid     (vii) IMMEDIATE SOURCE:
        (B) CLONE: AO677

(xi) SEQUENCE DESCRIPTION: SEQ ID NO:3:

TAAAGCTCGT CCCTCTTCAG     20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid     (vii) IMMEDIATE SOURCE:
        (B) CLONE: AO678

(xi) SEQUENCE DESCRIPTION: SEQ ID NO:4:

ATGTGCACTT GTATGGGCAG     20